United States Patent
Yamamoto et al.

(10) Patent No.: US 6,929,741 B2
(45) Date of Patent: Aug. 16, 2005

(54) COLUMN PACKAGING FOR CHROMATOGRAPHY

(75) Inventors: Eiichi Yamamoto, Ibaraki (JP); Kaoru Murata, Ibaraki (JP); Yasushi Ishihama, Ibaraki (JP); Naoki Asakawa, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 91 days.

(21) Appl. No.: 10/181,779

(22) PCT Filed: Feb. 9, 2001

(86) PCT No.: PCT/JP01/00947

§ 371 (c)(1),
(2), (4) Date: Jul. 22, 2002

(87) PCT Pub. No.: WO01/59444

PCT Pub. Date: Aug. 16, 2001

(65) Prior Publication Data

US 2003/0003311 A1 Jan. 2, 2003

(30) Foreign Application Priority Data

Feb. 10, 2000 (JP) .......................................... 2000-33554

(51) Int. Cl.⁷ .............................................. B01D 15/08
(52) U.S. Cl. ................................ 210/198.2; 210/502.1; 210/635; 210/656; 502/402
(58) Field of Search .................................. 210/635, 656, 210/659, 198.2, 502.1; 502/401, 402, 404

(56) References Cited

U.S. PATENT DOCUMENTS

| | | | | |
|---|---|---|---|---|
| 3,954,678 A | * | 5/1976 | Marquisee | 252/62.54 |
| 4,544,485 A | * | 10/1985 | Pinkerton et al. | 210/502.1 |
| 4,714,555 A | * | 12/1987 | Shibata et al. | 210/635 |
| 4,941,974 A | * | 7/1990 | Williams | 210/198.2 |
| 4,952,550 A | * | 8/1990 | Wallach et al. | 502/404 |
| 5,203,991 A | * | 4/1993 | Kutsuna et al. | 210/198.2 |
| 5,277,813 A | * | 1/1994 | Feibush et al. | 210/502.1 |
| 5,389,449 A | * | 2/1995 | Afeyan et al. | 428/523 |
| 5,672,422 A | * | 9/1997 | Kanda et al. | 428/304.4 |
| 6,040,472 A | * | 3/2000 | Yamamatsu et al. | 560/210 |
| 6,074,555 A | * | 6/2000 | Boos et al. | 210/198.2 |

FOREIGN PATENT DOCUMENTS

| | | |
|---|---|---|
| EP | 0 537 461 A1 | 4/1993 |
| EP | 0 635 301 A2 | 1/1995 |
| JP | 61-287444 A | 12/1986 |
| JP | 05-072190 A | 3/1993 |
| JP | 5-87790 | 4/1993 |
| JP | 05-203636 A | 8/1993 |
| JP | 05-302917 A | 11/1993 |

OTHER PUBLICATIONS

Translation of Japan Patent Application No. 5–302917, PTO 04–3062 Apr. 2004, pp. 1–18.*
Snyder, Introduction to Modern Liquid Chromatography, John Wiley & Sons, Inc., New York, 1979, p. 489.*
Mikes' Laboratory Handbook of Chromatographic and Allied Methods, Ellis Horwood Limited, 1979, Sussex, England, pp. 157–159.*
Jun Haginaka et al., Journal of Chomagography, vol. 515, pp. 59–66 (1990).
Stefan Vielhauen et el., Journal of Chomagography, vol. 666, pp. 315–322 (1995).
I. Helene Hagestam et al.; Anal. Chem., 1985, vol. 57, pp. 1757–1763.

* cited by examiner

*Primary Examiner*—Ernest G. Therkorn
(74) *Attorney, Agent, or Firm*—Birch, Stewart, Kolasch & Birch, LLP

(57) ABSTRACT

The present invention provides a packing for chromatography. Specifically, it provides a packing for chromatography in which a hydrophilic polymeric material is bound to the surface of a porous carrier, and a carbon chain is chemically bound inside the pore. By the use of the packing according to the present invention for analysis of low molecular weight compounds in a biological sample, a pretreatment such as removal of proteins etc. becomes unnecessary, and the biological sample can be directly analyzed.

20 Claims, 3 Drawing Sheets

Time (min)

(1) Blank (2) n-propyl p-hydroxy benzoate sample solution (load 100 ng) (3) BSA sample solution (load 20 mg) (4) a mixed sample solution of BSA (load 20 mg) and n-propyl p-hydroxy benzoate (load 100 ng)

(1) blank (2) rat plasma (300 μl) (3) a mixed sample solution of rat plasma (300 μl) and n-propyl p-hydroxy benzoate (load 100ng)

COLUMN PACKAGING FOR CHROMATOGRAPHY

This application is the national phase under 35 U.S.C. §371 of PCT International Application No. PCT/JP01/00947 which has an International filing date of Feb. 9, 2001, which designated the United States of America.

TECHNICAL FIELD

The present invention relates to packings for chromatography, more particularly it relates to packings for chromatography which allow direct analysis of trace amounts of components present in serum and the like.

PRIOR ART

Recently high-performance liquid chromatography has been widely employed for separation or for qualitative or quantitative analyses of various materials. Since its separating power depends largely on the column employed, various columns have been developed and commercially available. Particularly prevalent columns among them are those comprising a carrier such as silica gel having carbon chains bonded thereto, and are generally referred to as reversed-phase columns. By the way, the high performance liquid chromatography, having high separating power and high sensitivity, has been often used for quantitative analysis of biological components such as low molecular weight compounds contained in plasma and the like. However, biological components in plasma such as albumin are likely to be adsorbed to the column, particularly when a reversed-phase type column is employed, resulting in a lowering the separating power of the column and increasing the pressure required for sending the solvent. Therefore, pretreatments have been required so far for removing the plasma protein and the like. In order to overcome these defects, Pinkerton et al. have developed a column comprising a porous silica gel support in which only the inside is chemically modified (Anal. Chem. 1985, Vol. 57, pp. 1757–1763).

The column developed by Pinkerton et al. is superior in eliminating the interference of the biological component during the analysis, but it is not sufficiently satisfactory from the viewpoints of retention of the low molecular weight compounds by the column, separating power and durability of the column. There are other columns such as those disclosed in JP-A 5-87790, which have been developed for similar purposes as the column developed by Pinkerton et al., but they are not satisfactory either. In addition to that, these columns including the ones developed by Pinkerton et al. are expensive since they have been produced in complicated production processes.

DISCLOSURE OF THE INVENTION

The present inventors have extensively studied on a packing and a column packed with such a packing which can avoid the interference of biological components and show sufficient retentive and separating capacities, and have found that the defects of the conventional columns can be solved with the construction shown below, and completed the present invention.

The present invention relates to a packing for chromatography comprising a porous carrier with the surface bonded to a hydrophilic polymeric material, and a carbon chain chemically bonded to inside of the pore. The present invention also relates to a column packed with a packing for chromatography comprising a porous carrier with the surface bonded to a hydrophilic polymeric material, and a carbon chain chemically bonded to inside of the pore. The present invention further relates to a method of analyzing or separating trace amounts of components by injecting whole blood, plasma or serum into a column packed with a packing for chromatography comprising a porous carrier with the surface bonded to a hydrophilic polymeric material, and a carbon chain chemically bonded to inside of the pore. The present invention further relates to a use of a packing comprising a porous carrier with the surface bonded to a hydrophilic polymeric material, and a carbon chain chemically bonded to inside of the pore, as a packing for chromatography.

When a packing for chromatography according to the present invention is employed for analysis of low molecular weight compounds in a biological sample, pretreatment such as protein removal and the like becomes unnecessary, the analysis of the biological components can be directly carried out, the analytical method is simplified and the time required for analysis is shortened. To provide such a packing is an object of the present invention.

A porous carrier according to the present invention includes silica gel, cellulose, agarose and a synthetic polymer, having a particle diameter of generally 2 to 100 µm. As the carrier has many pores dented from the surface, it has a large specific surface area.

A hydrophilic polymeric material means a polymeric substance having a hydrophilic group such as hydroxyl group having a molecular weight of from 1,000 to 2,000,000, and examples thereof include methyl cellulose, ethyl cellulose, hydroxy propyl cellulose, polyvinyl pyrolidone and hexadimethrine bromide.

"A carrier with the surface bonded to a hydrophilic polymeric material" according to the present invention refers to a carrier wherein a hydrophilic polymeric material is physically or chemically bonded to the surface of the carrier and it is not substantially bonded to inside of the pores of the carrier.

A part or all of the functional groups of a hydrophilic polymeric material according to the present invention may be chemically modified. Examples of chemical modification include glycolization, reduction and carboxylation to introduce two carboxyl groups. Glycolization refers to reactions, in which, for example, the cyclic moiety of the methacryloxy ring is treated with an acid such as diluted sulfuric acid to form two hydroxy groups.

A carbon chain bonded to inside of the pore of the carrier according to the present invention includes a linear or branched carbon chain optionally modified with a cyano, allyl, aryl, amino, carboxylic acid, sulfonic acid, or sulfuric acid group and the like, and the carbon chain is chemically bonded to the carrier by an ester bond, ether bond, or amide bond and the like. Modification of the carbon chain can be carried out, for example, by a process in which a sililation reagent having a carbon chain is dissolved in an organic solvent such as toluene, cyclohexane, and tetrahydrofuran, and silica gel in which a carbon chain is bonded to inside of the pore, is added thereto to have the carbon chain chemically modified.

The carbon chain may be linear or branched and the number of the carbon atoms in the carbon chain is 1 to 30.

The carbon chain is introduced from a compound having such a carbon chain; examples thereof include chlorosilane having $C_4$–$C_{12}$, and octadecyltrichlorosilane, a substance used for introducing an ion exchange group.

These carbon chains are chemically bonded to inside of the pores, which are open on the surface of the carrier.

The pore diameter is preferably between 50 and 500 Å.

Packings for chromatography according to the present invention can be produced, for example, by the following process. A 0.2 w/v % aqueous solution of polybrene (hexadimethrine bromide) is added to silica gel and stirred for about 1 hour. It is filtered through a glass filter, washed with water, and dried at about 130° C. for about 1 hour to give a carrier wherein polybrene is bonded to the surface of silica gel. Hexane and triethylamine are added thereto, and octadecyltrichlorosilane is added gradually under stirring, then the reactants are stirred for about 30 minutes, then ethanol is added. The obtained carrier is filtered through a glass filter, washed with ethanol and dried at about 130° C. for about 1 hour to give a packing according to the present invention. By packing the obtained packing into a column cartridge, a column according to the present invention can be produced. The column cartridge is normally made of stainless steel when used for HPLC analysis, however, when it is independently used for trapping trace amounts of substances contained in biological components, a column made of a synthetic resin can be used as well.

DESCRIPTION OF THE PREFERRED EMBODIMENTS

When a biological sample is directly injected into a column according to the present invention, macromolecule species such as a protein in the biological sample are excluded by the hydrophilic polymer on the surface of the packing, and flow through the column without reaching the carbon chain in the pores. On the other hand, low molecular weight compounds pass through the hydrophilic polymeric material on the surface of the packing and reach the pore of the packing and are retained by the carbon chains in the pore. Therefore, an analysis can be carried out without being affected by the macromolecular species such as a protein in the biological sample, and only the low molecular weight compounds are well retained and separated.

Figure 1:
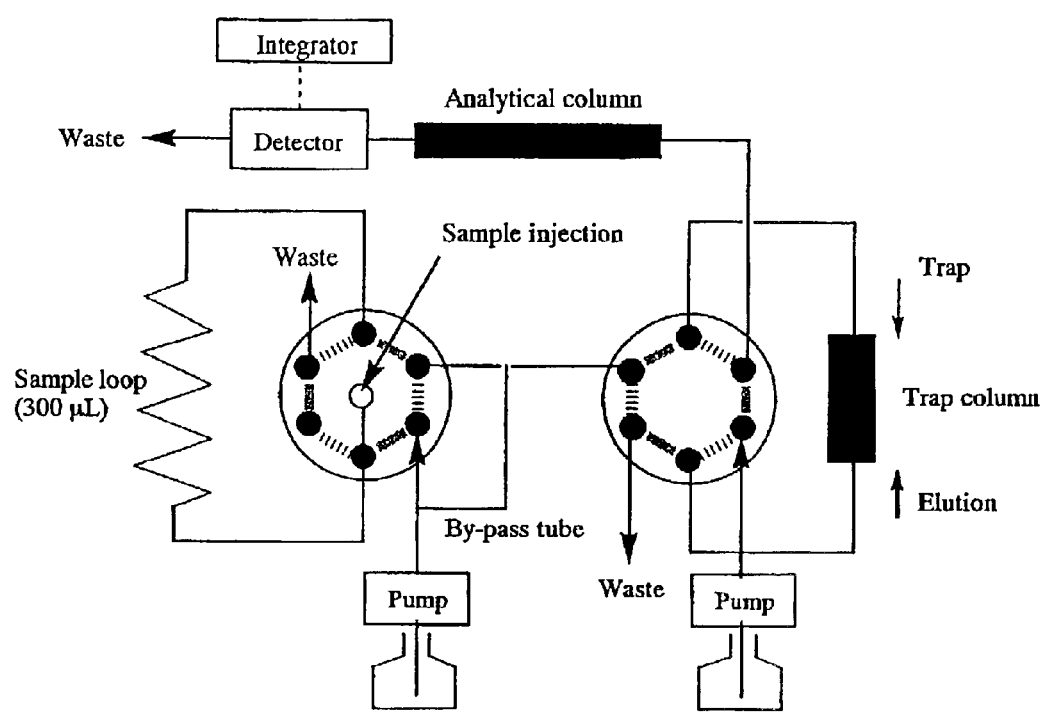
FIG. 1 is a diagram of HPLC system, which was used for evaluation of the present invention.

The effect of the present invention is shown below by Test Example using a column obtained in Example 1.
1. Apparatus
Pump: LC-5A, LC-9A (fabricated by Shimadzu Corporation)
UV detector: 870-UV (fabricated by JASCO)
Integrator: LC-4AX (fabricated by Shimadzu Corporation)
Sample Injector: 7125 (fabricated by Rheodyne)
HPLC flow path-switching valve: 7000 (fabricated by Rheodyne)
Column Cartridge: 4.6 mm (i.d.)×10 mm (fabricated by GL Science)
Analytical Column: ULTRON VX-ODS (5 $\mu$m) 4.6 mm (i.d.)×150 mm (fabricated by Shinwa Kako Corporation)
2. Sample Solution
Blank solution: Ultrapure water was employed.
BSA sample solution: 1000 mg of BSA was weighed and 5.0 ml of a 0.5% ammonium acetate solution was added thereto, to prepare a BSA sample solution (BSA concentration was 200 mg/ml; BSA is an abbreviation of bovine serum albumin (protein)).
p-Hydroxybenzoic acid n-propyl ester sample solution: 10 mg of p-hydroxybenzoic acid n-propyl ester was weighed, 1 ml of ethanol was added thereto and 9 ml of ultrapure water was added and the obtained solution was further diluted 100 times with the ultrapure water, to give a sample solution (10 $\mu$m/ml).
3. Procedure As the apparatus, a column switching HPLC apparatus shown in FIG. 1 was employed. The procedure was carried out as follows.

(1) An aliquot of the sample solution was injected into the sample loop using a syringe and a sample injector valve was switched, and the sample was introduced by the mobile phase of the trap HPLC system into the trap column.

(2) The mobile phase was pumped to flow for 10 minutes to remove the protein contained in the sample.

(3) The flow switching valve was switched to send the moving phase of the analytical HPLC system into the trap column, to allow the desired component to be eluted from the trap column and introduced into the analytical column, then the resulting chromatogram was recorded.
4. Test Conditions An aliquot of the sample was injected with a syringe and the effects of the column according to the present invention were tested under the following conditions.
HPLC Conditions
Trap System
Column: A column according to the present invention 4.6 mm (i.d.)×10 mm
Moving phase: 0.5% ammonium acetate solution
Flow rate: a constant rate around 1.0 ml/min
The amount of the sample injected: 100–300 $\mu$l of BSA sample solution (20–60 mg of BSA contained), 10 $\mu$l of hydroxy benzoic acid n-propyl ester sample solution (100 ng)
Trap time: 10 min
Analytical System
Column: ULTRON VX-ODS (5 $\mu$m) 4.6 mm(i.d.)×250 mm
Moving phase: 45% acetonitrile solution containing 0.2% TFA
Flow rate: a constant flow rate around 1.0 ml/min
Detection wave length: UV 254 nm
Analytical time: 10 min
5. Results Chromatograms of (1) blank solution, (2) p-hydroxy benzoic acid n-propyl ester sample solution (load 100 ng), (3) BSA solution (load 20 mg) and (4) BSA and p-hydroxy benzoic acid n-propyl ester mixed sample solution (loads were 20 mg and 100 ng respectively) are shown in FIG. 2.

Figure 2:
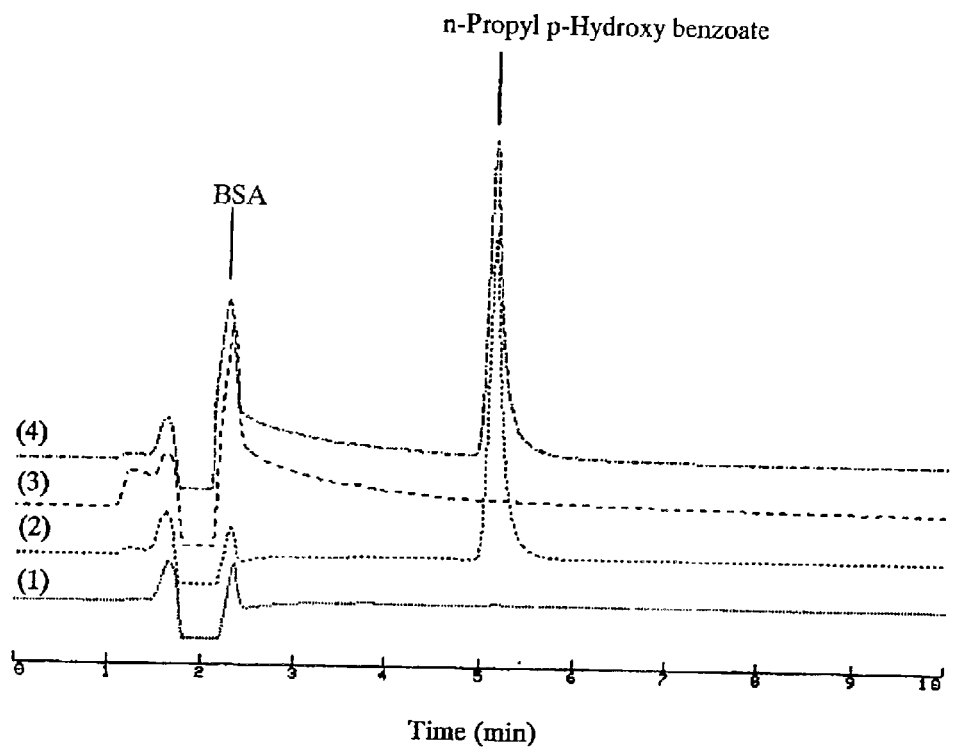
FIG. 2 is a chromatogram obtained by using a packing according to the present invention.

FIG. 2 shows that the injected BSA (protein) was not adsorbed on the surface of the packing, and the protein was deemed to be excluded since the surface of the packing is modified with the hydrophilic group (chromatogram (3)). As the p-hydroxy benzoic acid ester is retained in the packing according to the present invention due to the hydrophobic interaction, the inside of the packing is deemed to be modified with a carbon chain (chromatogram (2)). When a mixed sample solution containing BSA and p-hydroxy benzoic acid n-propyl ester was injected, p-hydroxy benzoic acid n-propyl ester was detected without being interfered by the BSA (chromatogram (4)).

Figure 3:
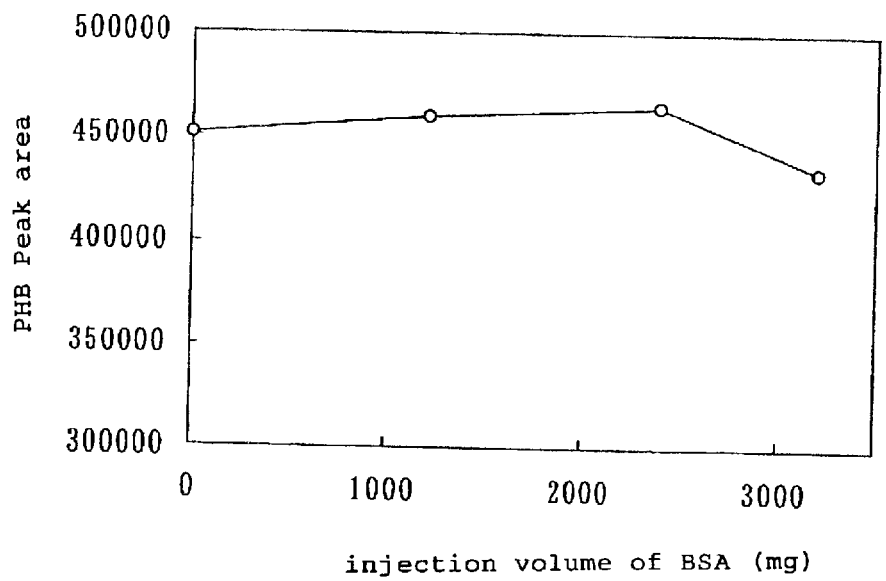
FIG. 3 is a graph showing the change in p-hydroxy benzoic acid (PHB) peak area obtained by continuously injecting a protein (BSA) into a packing according to the present invention.

A graph showing the retention capacity of the trap column into which the BSA solution was repeatedly injected is given in FIG. 3. FIG. 3 clearly shows that the performance of the trap column is not deteriorated by injection of a large amount of BSA.

Figure 4:
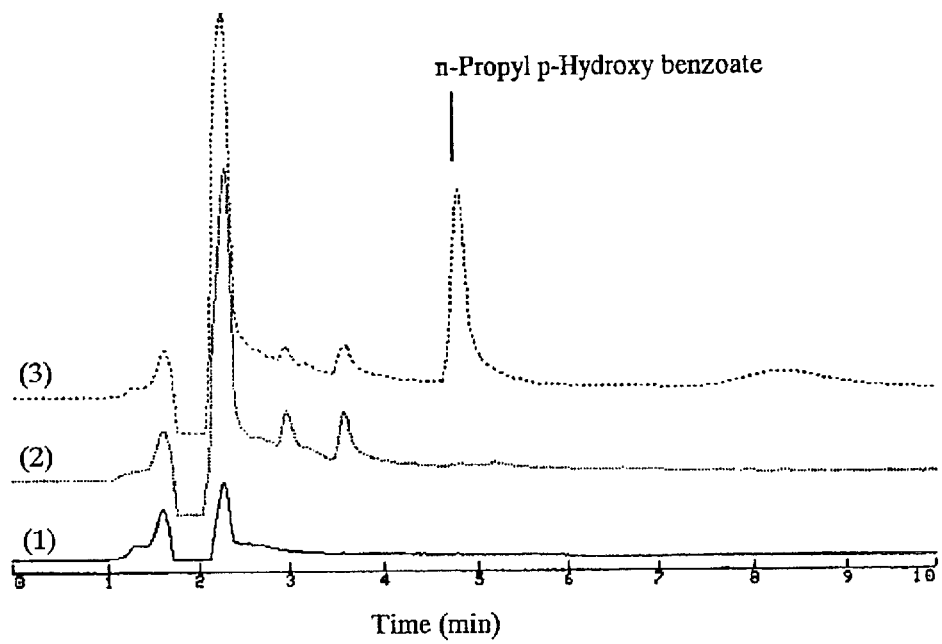
FIG. 4 is a chromatogram obtained by injecting rat plasma into a packing according to the present invention and to a packing being commercially available.

FIG. 4 shows chromatograms of a sample (300 $\mu$l), supernatant of rat plasma centrifuged at 1000 rpm for 30 minutes, which was obtained with a commercially available column (the surface of the carrier is modified with octyldecyl group) and a column according to the present invention.

When the plasma is injected into the commercially available column, it is retained in the column resulting in large tailing (chromatogram (3)), that makes the detection of trace amounts of substances in the plasma extremely difficult, while the chromatogram obtained with the column according to the present invention is free from any tailing since the plasma is not retained in the column, therefore it is suited for micro analysis of the plasma.

From the above-mentioned results, it is confirmed that the serum direct injection column packing according to the present invention excludes the BSA to a great extent through the hydrophilic polymeric material on the external surface of the packing, and the ODS chain on the inner surface of the packing has sufficient retention capacity. Even after a protein is injected, in an amount of 3000 mg or more as BSA, both the trap column and the analytical column showed no reduction in column performance and no remarkable increase in the column pressure was observed for sending the solutions.

EXAMPLES

The present invention will be described in more detail by the following Examples, but the present invention is not limited by them.

Example 1

To 1 g of silica gel was added 30 ml of a 0.2 w/v % polybrene (hexadimethrine bromide) aqueous solution, followed by stirring for about 1 hour. It was filtered through a glass filter, washed with water, and then dried at 130° C. for 1 hour, to give a carrier in which polybrene was bound to the surface of silica gel. 30 ml of hexane and 0.3 ml of triethylamine were added thereto, and 0.5 ml of octadecyltrichlorosilane was gradually added thereto under stirring. After stirring for about 30 minutes, 10 ml of ethanol was added. The resulting carrier was filtered through a glass filter, washed with ethanol and then dried at 130° C. for 1 hour, to give a packing according to the present invention.

Example 2

To 1 g of silica gel was added 30 ml of a 0.2 w/v % methyl cellulose aqueous solution, followed by stirring for about 1 hour. It was filtered through a glass filter, washed with water and dried at 130° C. for 1 hour, to give a carrier in which methyl cellulose was bonded to the surface of silica gel. 30 ml of hexane and 0.3 ml of triethylamine were added thereto, and 0.5 ml of octadecyltrichlorosilane was gradually added thereto under stirring. After stirring for about 30 minutes, 10 ml of ethanol was added. The resulting carrier was filtered through a glass filter, washed with ethanol and then dried at 130° C. for 1 hour, to give a packing according to the present invention.

Examples 3

To the packing obtained in Example 1 was added 20 ml of a 0.1% aqueous alginic acid solution and stirred. The mixture was washed with water and then filtered, to give a packing in which a hydrophilic polymeric material is modified.

What is claimed is:

1. A packing for chromatography in which a hydrophilic polymeric material is bound to a surface of a porous silica gel, and a carbon chain is chemically bound inside the pore of the silica gel, wherein said packing is prepared by a step of contacting the pore of the silica gel with a compound having said carbon chain.

2. The packing for chromatography according to claim 1, in which the hydrophilic polymeric material has a molecular weight of from 1,000 to 2,000,000.

3. The packing for chromatography according to claim 1, in which the hydrophilic polymeric material is methyl cellulose, ethyl cellulose, hydroxypropyl cellulose, polyvinylpyrrolidone or hexadimethrine bromide.

4. The packing for chromatography according to claim 1, in which the carbon chain is a linear or branched carbon chain optionally modified with a cyano group, allyl group, aryl group, amino group, carboxylic acid group, sulfonic acid group or sulfuric acid group.

5. The packing for chromatography according to claim 4, in which the number of the carbon atoms in the linear or branched carbon chain is from 1 to 30.

6. The packing for chromatography according to claim 1, in which the hydrophilic polymeric material is a chemically modified hydrophilic polymeric material.

7. The packing for chromatography according to claim 6, in which the chemical modification is glycolization, reduction or carboxylation to introduce two carboxyl groups.

8. The packing for chromatography according to claim 1, in which the compound having said carbon chain is a $C_4$–$C_{12}$ chlorosilane, an octadecyltrichlorosilane or a substance used for introducing an ion exchange group.

9. The packing for chromatography according to claim 8, in which the carbon chain is a linear or branched carbon chain optionally modified with a cyano group, allyl group, aryl group, amino group, carboxylic acid group, sulfonic acid group or sulfuric acid group.

10. A column packed with the packing for chromatography according to claim 1.

11. A packing for chromatography in which a hydrophilic polymeric material is bound to a surface of a porous silica gel, and a carbon chain is chemically bound inside the pore of the silica gel, wherein said packing is prepared with a compound having the carbon chain.

12. The packing for chromatography according to claim 11, in which the hydrophilic polymeric material has a molecular weight of from 1,000 to 2,000,000.

13. The packing for chromatography according to claim 11, in which the hydrophilic polymeric material is methyl cellulose, ethyl cellulose, hydroxypropyl cellulose, polyvinylpyrrolidone or hexadimethrine bromide.

14. The packing for chromatography according to claim 11, in which the carbon chain is a linear or branched carbon chain optionally modified with a cyano group, allyl group, aryl group, amino group, carboxylic acid group, sulfonic acid group or sulfuric acid group.

15. The packing for chromatography according to claim 14, in which the number of the carbon atoms in the linear or branched carbon chain is from 1 to 30.

16. The packing for chromatography according to claim 11, in which the hydrophilic polymeric material is a chemically modified hydrophilic polymeric material.

17. The packing for chromatography according to claim 16, in which the chemical modification is glycolization, reduction or carboxylation to introduce two carboxyl groups.

18. The packing for chromatography according to claim 11, in which the compound having said carbon chain is a $C_4$–$C_{12}$ chlorosilane, an octadecyltrichlorosilane or a substance used for introducing an ion exchange group.

19. The packing for chromatography according to claim 18, in which the carbon chain is a linear or branched carbon chain optionally modified with a cyano group, allyl group, aryl group, amino group, carboxylic acid group, sulfonic acid group or sulfuric acid group.

20. A column packed with the packing for chromatography according to claim 11.

* * * * *